United States Patent
Margolin

(10) Patent No.: US 9,664,688 B2
(45) Date of Patent: May 30, 2017

(54) METHOD OF IDENTIFYING RISK FOR THYROID DISORDER

(71) Applicant: Genzyme Corporation, Cambridge, MA (US)

(72) Inventor: David H. Margolin, Somerville, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 13/705,944

(22) Filed: Dec. 5, 2012

(65) Prior Publication Data

US 2013/0095507 A1    Apr. 18, 2013

Related U.S. Application Data

(63) Continuation of application No. 12/526,129, filed as application No. PCT/US2008/002047 on Feb. 15, 2008, now abandoned.

(60) Provisional application No. 60/901,732, filed on Feb. 16, 2007.

(51) Int. Cl.
G01N 33/50 (2006.01)
G01N 33/68 (2006.01)

(52) U.S. Cl.
CPC ..... *G01N 33/6854* (2013.01); *G01N 33/5047* (2013.01); *G01N 33/6893* (2013.01); *G01N 2333/635* (2013.01); *G01N 2333/70592* (2013.01); *G01N 2800/046* (2013.01)

(58) Field of Classification Search
None
See application file for complete search history.

(56) References Cited

U.S. PATENT DOCUMENTS

| 5,846,534 A | 12/1998 | Waldmann et al. |
| 6,120,766 A | 9/2000 | Hale et al. |
| 2008/0267954 A1 | 10/2008 | Margolin et al. |
| 2013/0108625 A1 | 5/2013 | Margolin |

FOREIGN PATENT DOCUMENTS

GB    2 265 713 A    10/1993

OTHER PUBLICATIONS

Hale et al., Bone Marrow Transplantation, 2000; 26, 69-76.*
Anderson et al., Journal of Immunol., 1977; 118: 1191-1200.*
Prummel et al., European Journal of Endocrinology, 2004; 150: 605-618.*
Coles et al., N Engl J Med. 2008; 359: 1786-1801.*
Petek-Balci et al., "Multiple Sclerosis and Hashimoto Thyroiditis Two Cases," Neurologist, 11:301-304 (2005).
"Handbook of diagnosis and differential diagnosis laboratory medicine," Vincent Marks, Dusan Mesko, Springer, Berlin, Germany, pp. 100-104 (2002).
Carlson K., et al., "Thyroid Function After Autologous Bone Marrow Transplantation," *Bone Marrow Transplant.*, 10(2):123-127 (1992).
Coles, A. J., et al., "CAMPATH-1H Treatment of Multiple Sclerosis," *Neurology* 60, p. A168, (2003).
Coles, A. J., et al., "Monoclonal Antibody Treatment Exposes Three Mechanisms Underlying the Clinical Course of Multiple Sclerosis," *American Neurological Association*, 46(3):296-304 (1999).
Coles, A. J., et al., "CAMPATH-1H Treatment of Multiple Sclerosis: lessons from the Bedside for the Bench," *Clinical Neurology and Neurosurgery*, 106:270-274 (2004).
Coles, A. J., et al. "Pulsed Monoclonal Anitbody Treatment and Autoimmune Thyroid Disease in Multiple Sclerosis," *The Lancet*, 354:1691-1695 (1999).
Compston, D.A.S., et al., "Two Year Interim Analysis of Thyroid Abnormalities in a Trial of Alemtuzumab vs. High-Dose Interferon-Beta-1a, for Treatment of Relapsing-Remitting Multiple Sclerosis," Presented at the 22$^{nd}$ meeting of the European Committee for Treatment and Research in Multiple Sclerosis (ECTRIMS), Madrid, Spain. Sep. 27 to 30, 2006.
Fernandez-Soto, L., et al., "Increased Risk of Autoimmune Thyroid Disease in Hepatitis C vs. Hepatitis B Before, During, and After Discontinuing Interferon Therapy," *Arch Intern Med*, 158(13):1445-1448 (1998).
Fox, E., et al., "Ongoing Evaluation of the Safety and Tolerability of Novantrone® (Mitoxantrone Worsening Multiple Sclerosis: The RENEW Study," Presented at the ECTRIMS, Madrid, Spain (2006).
Fox, E., et al., "ITP Following Treatment of Multiple Sclerosis Patients with Alemtuzumab in CAMMS223: Case Reports and Risk Management Plan Implementation," Presented at the ECTRIMS, Madrid, Spain (2006).
Hale G, et al., "The CAMPATH-1 Antigen (CDw52)," *Tissue Antigens*, 35:118-127 (1990).
Hale G. and Waldmann H., "From Laboratory to Clinic: The Story of CAMPATH-1," *Methods in Molecular Medicine: Diagnostic and Therapeutic Antibodies* 40:243-266 (2000).
Ishiguro H., et al., "Long-Term Follow-Up of Thyroid Function in Patients Who Received Bone Marrow Transplantation During Childhood and Adolescence," *J Clin Endocrinol Metab*, 89(12):5981-5986 (2004).

(Continued)

*Primary Examiner* — Christina Borgeest
(74) *Attorney, Agent, or Firm* — Steptoe & Johnson LLP; Z. Ying Li; Wyan-Ching M. Lee

(57) ABSTRACT

A method for identifying a patient that is at risk for developing a thyroid disorder that occurs subsequent to treatment with a regimen that depletes lymphocytes, comprising determining whether antibodies directed against thyroid peroxidase or thyroid microsomes are present in the patient, wherein if the antibodies are present in the patient then the patient is at increased risk for developing a thyroid disorder. A particular embodiment is a method for identifying a patient with multiple sclerosis that is at risk for developing a thyroid disorder that occurs subsequent to treatment with a regimen that depletes CD52-positive cells, comprising determining whether antibodies directed against thyroid peroxidase or thyroid microsomes are present in the patient, wherein if the antibodies are present in the patient then the patient is at risk for developing the thyroid disorder.

5 Claims, No Drawings

(56) References Cited

OTHER PUBLICATIONS

Kung, V.T. et al., "Double-Antibody Radioimmunoassay of Thyroid Microsomal Antibody in Serum," *Clin. Chem.*, 27(1):39-42(1981).
Lee W.Y., et al., "Changes in Autoimmune Thyroid Disease Following Allogeneic Bone Marrow Transplantation," *Bone Marrow Transplant.*, 28(1):63-6. (2001).
Marazuela, M., et al., "Thyroid Autoimmune Disorders in Patients with Chronic Hepatitis C Before and During Interferon-α Therapy," *Clin Endocrinol* 44:635-42 (1996).
O'Donnell, L, et al, "Safety and Management of CAMPATH-1H Infusion Reactions in MS Patients," *Presented at the Consortium of Multiple Sclerosis Centers Annual Meeting*, Toronto, Canada, Jun. 2-6, 2004.
Premawardhana, L.D.K.E., et al., "Postpartum Thyroiditis and Long-Term Thyroid Status: Prognostic Influence of Thyroid Peroxidase Antibodies and Ultrasound Echogenicity," *J. Clin. Endocrinol. Metab.*, 85(471-75 (2000).
Preziati, D., et al., "Autoimmunity and Thyroid Function in Patients with Chronic Active Hepatitis Treated with Recombinant Interferon Alpha-2a," *Eur J Endocrinol*, 132(5)587-593 (1995).
Slatter M.A., et al., "Thyroid Dysfunction After Bone Marrow Transplantation for Primary Immunodeficiency Without the Use of Total Body Irradiation in Conditioning," *Bone Marrow Transplant.*, 33(9):949-953 (2004).
Stagnaro-Green, A., et al., "A Prospective Study of Lymphocyte-Initiated Immunosuppression in Normal Pregnancy: Evidence of a T-Cell Etiology for Postpartum Thyroid Dysfunction," *J. Clin. Endocrinol Metab.*, 74(3): 645-653 (1992).
Sundbeck, G., et al., "Prevalence of Serum Antithyroid Peroxidase Antibodies in 85-Year-Old Women and Men," *Endocrinology and Metabolism, Clinical Chem.*, 41(5): 707-712 (1995).
T. Moreau, et al., "Transient Increase in Symptoms Associated With Cytokine Release in Patients With Multiple Sclerosis," *Brain*, 119:225-237 (1996).
T. Moreau, et al., "Preliminary Evidence From Magnetic Resonance Imaging for Reduction in Disease Activity After lymphocyte Depletion in Multiple Sclerosis," *Lancet*, 344: 298-301 (1994).
Vargas, M.T., et al., "Antithyroid Microsomal Autoantibodies and HLA-DR5 Are Associated With Postpartum Thyroid Dysfunction: Evidence Supporting an Autoimmune Pathogenesis*," *J. Clin. Endocrinol. Metab.*, 67(2):327-33 (1988).

Watanabe, U., et al., "The Risk Factor for Development of Thyroid Disease During Interferon-α Therapy for Chronic Hepatitis C," *Am J Gastroenterol.*, 89(3):399-403 (1994).
Balan, K.K., et al., "Thyroid Dysfunction Following Anit-Lymphocyte Monoclonal Antibody Treatment of Multiple Sclerosis—Scintgraphic Assessment", *J. Nuclear Med., Proceedings of the 45th Annual Meeting*, 39(5 Supp.):263P, No. 1156 (May 1998).
McLachlan, S., et al., "The Link Between Graves' Disease and Hashimoto's Thyroiditis: A Role for Regulatory T Cells", *Endocinology*, 148(12):5724-5733 (Dec. 2007).
Gillard, P., et al., "Graves Hyperthyroidism After Stopping Immunosuppressive Therapy in Type 1 Diabetic Islet Cell Recipients with Pretransplant TPO Autoantibodies", *Diabetes Care*, 32(10):1817-1819 (Oct. 2009).
Daneshpazhooh, M., et al., "Anti-Thyroid Peroxidase Antibody and Vitiligo: A Controlled Study", *BMC Dermatol*, 6: 1-5 (2006).
Dupont, E., et al., "Depletion of Lymphocytes With Membrane Markers of Helper Phenotype: A Feature of Acute and Chronic Drug-Induced Immunosuppression", *Clin. Exp. Immunol.*, 51: 345-350 (1983).
Anderson, R.E., et al., "Radiosensitivity of T and B Lymphocytes: IV. Effect of Qhole Body Irradiation Upon Various Lymphoid Tissues and Numbers of Recirculating Lymphocytes", *J. Immunol.*, 118: 1191-1200 (1977).
Erickson, S., et al., "Interferon-α Inhibits Proliferation in Human T Lymphocytes by Aborgation of Interleukin 2-Induced Changes in Cell-Regulatory Proteins", *Cell Growth & Differentiation*, 10: 575-582 (1999).
Keating, M. J., et al., "Therapeutic Role of Alemtuzumab (Campath-1H) in Patients Who Have Failed Fludarabine: Results of a Large International Study", *Blood*, 99: 3554-3561 (2002).
Aug. 27, 2009, Notification Concerning Transmittal of International Preliminary Report on Patentability (Chapter 1 of the Patent Cooperation Treaty), PCT/US2008/002047.
Jul. 10, 2008, Notification of Transmittal of the International Search Report and the Written Opinion of the International Searching Authority, or the Declaration, PCT/US2008/002047.
Apr. 2, 2010, Examiner's First Report, 2008219097.
Jul. 6, 2010, Office Action, 08725657.4.
Jul. 17, 2011, Notification of Defects in Patent Application, 200314.
Swain et al., "Autoimmune thyroid disorders—An Update," Indian Journal of Clinical Biochemistry, 20(1):9-17 (2005).
Wu et al., "The Clinical Significance of Identifying Antibodies Directed Against Thyroid Peroxidase in a Subject Suffering Autoimmune Thyroid Disorder," Journal of Clinical Internal Medicine, 19:124-125 (2002) (English Translation).

\* cited by examiner

METHOD OF IDENTIFYING RISK FOR THYROID DISORDER

RELATED APPLICATIONS

This application is a continuation of U.S. application Ser. No. 12/526,129, which is the U.S. National Stage Application of International Application No. PCT/US2008/002047 filed on Feb. 15, 2008, published in English, which claims the benefit of U.S. Provisional Application No. 60/901,732, filed on Feb. 16, 2007. The entire teachings of the above applications are incorporated herein by reference.

BACKGROUND OF THE INVENTION

A major function of the thyroid gland is to secrete the thyroid hormones L-thyroxine (T4) and L-triiodothyronine (T3). These thyroid hormones regulate important aspects of metabolism. A state of hypothyroidism exists when the blood levels of T3 and T4 are abnormally low, and hyperthyroidism exists when their levels are abnormally elevated. Untreated, severe hypothyroidism is characterized by weight gain, low energy and depression, intolerance of cold, and changes in skin and hair. Untreated, severe hyperthyroidism presents as a state called thyrotoxicosis, characterized by weight loss, nervousness or emotional instability, intolerance of heat, tremor, and a rapid heart rate, and can cause cardiac atrial fibrillation. In some cases hypothyroidism or hyperthyroidism may occur with no discernible symptoms or signs despite abnormal findings on laboratory tests of thyroid function (e.g., a subclinical thyroid disorder).

T3 and T4 are produced under direct control by the anterior pituitary glycoprotein hormone thyrotropin (thyroid stimulating hormone, TSH), which is itself regulated by the hypothalamic hormone thyrotropin releasing hormone (TRH). TSH acts through a membrane-bound G-protein coupled receptor (TSH-R) to activate the major thyroidal functions. Synthesis of T3 and T4 requires incorporation of iodide into their precursor. Thyroid peroxidase (TPO) is a membrane-bound, glycosylated heme-containing enzyme that catalyzes both the iodination of tyrosyl residues and the coupling of iodotyrosyl residues in thyroglobulin to form T3 and T4. Once synthesized, T3 and T4 are stored in a colloidal form on the protein thyroglobulin (Tg) prior to release of the hormones.

Under pathological conditions, the TPO, TSH-R, and Tg proteins may become autoantigens, i.e., targets for autoimmune responses most easily identified by the auto-antibodies that bind these proteins. Historically, antibodies reactive with the microsomal fraction of thyroid tissue were also detected and studied. Later, thyroid peroxidase was found to be the chief target for such anti-thyroid microsomal antibodies. With this understanding, thyroid microsomal antibodies and thyroid peroxidase antibodies have been considered to be essentially equivalent terms.

The signaling function of the TSH-R protein normally becomes activated only upon binding of thyrotropin. However, some antibodies directed against the TSH-R (hereafter, TSHRA) may bind at the thyrotropin docking site, and this class of TSHRA autoantibody can act as a direct agonist (stimulating antibody) or antagonist (blocking antibody) of the TSH-R. Thus, thyroid autoimmunity can be associated with aberrant regulation of thyroid hormone secretion and cause either hypo- or hyper-thyroidism.

A common diagnostic finding in patients with the disorder variously known as Graves' disease, diffuse toxic goiter, von Basedow's disease, or Parry's disease is the presence of TSHRA in the blood. Antibodies directed against TPO (hereafter, TPOA) may be present or absent in Graves' disease. As explained above, patients with this disorder may present clinically with either hypo- or hyper-thyroidism, and a given patient may at different times manifest both conditions. In addition to thyroid dysfunction, the disorder may involve other tissues. In Graves' ophthalmopathy (technically an orbitopathy, because the changes are confined to orbital structures and spare the internal structure of the eye), enlargement of the extraocular muscle bundles and adipose hypertrophy cause protrusion of the eyeball (exophthalmos or proptosis) resulting in double vision (diplopia) and, in severe cases, visual loss. Some patients develop a dermopathy characterized by edema and thickening of the skin, or thickening of the finger bones. Hyperthyroid Grave's disease can often be managed with oral thyroid suppressant drugs, such as methimazole or propylthiouracil. Refractory cases may require thyroid ablation using radioactive iodine or a surgical thyroidectomy. With thyroid suppression, the patient will require thyroid replacement hormone. Severe ophthalmopathy may require radiation therapy delivered to the orbits or surgical decompression of the orbit.

Autoimmune thyroiditis is commonly known among endocrinologists as "silent thyroiditis" and Hashimoto's thyroiditis. TPOA are commonly present in patients with this disorder; high levels of TPOA in the context of the clinical presentation of hypothyroidism is often taken as confirmation for the diagnosis of Hashimoto's disease. TSHRA are usually absent. In this disorder, immune-mediated damage to the thyroid gland may lead to leakage of stored hormone with associated transient thyrotoxicosis, but commonly eventuates in an underactive thyroid gland with associated hypothyroidism. Treatment usually involves thyroid replacement hormone.

Certain disease states or therapeutic interventions are associated with an increased risk for autoimmune thyroid disorders. For example, thyroid disorders occur frequently among patients who receive interferon-alpha therapy for hepatitis C virus infection (Preziati, D., et al., *Eur J Endocrinol*, 132(5)587-93 (1995)). Among patients with hepatitis C virus infection, pretreatment antibodies to TPO or to thyroid microsomal fraction (a portion of which are known to recognize TPO) appear to be a marker for increased risk of hyper- and hypothyroid disorders among patients who subsequently receive interferon-alpha therapy (Marazuela, M., et al., *Clin Endocrinol* 44:635-42 (1996); Watanabe, U., et al., *Am J Gastroenterol*, 89(3):399-403 (1994); Fernandez-Soto, L.,et al., *Arch Intern Med*, 158:1445-1448 (1998)). Similarly, TPOA detected during pregnancy appear to predict risk for post-partum thyroid disorders (Vargas, M. T., et al., *J. Clin. Endocrinol. Metab.*, 67(2):327-33 (1988)).

Autoimmune thyroid disorders also occur with increased frequency among patients who have previously received lymphocyte depleting therapies. One such therapy is alemtuzumab. Alemtuzumab (Campath®, MabCampath®, Campath-1H®) is a humanized monoclonal antibody that binds selectively with the protein antigen known as CD52. CD52 is an abundant molecule (approximately $5 \times 10^5$ antibody binding sites per cell) present on at least 95% of all human peripheral blood lymphocytes and monocytes/macrophages (Hale G, et al., The CAMPATH-1 antigen (CD52). Tissue Antigens;35:178-327 (1990)), but is absent from haemopoietic stem cells. Treatment of a person with alemtuzumab using an appropriate dosage and regimen will, among other effects, result in prompt and relatively sustained depletion from the bodily tissues and blood of normal and neoplastic lymphocytes while sparing the haemopoietic stem cells that are needed to repopulate the immune system. Alemtuzumab is disclosed in U.S. Pat. No. 5,846,534.

Alemtuzumab is approved for the treatment of B-cell chronic lymphocytic leukemia (B-CLL) in patients who have been treated with alkylating agents and who have failed fludarabine therapy. Clinical studies have shown that alemtuzumab is also active in other hematologic malignancies such as non-Hodgkin's lymphoma and leukemias, and in a variety of immune mediated disorders including graft-versus-host disease, organ transplant rejection, rheumatoid arthritis, and, notably multiple sclerosis (Hale G. and Waldmann H., From laboratory to clinic: the story of CAMPATH-1. In: George A J T, Urch C E, eds. Methods in Molecular Medicine: Diagnostic and Therapeutic Antibodies. NJ: Humana Press; 2000; 40:243-266).

Hale and Waldmann were the first to disclose the use of Campath-1H to treat multiple sclerosis (MS) (see U.S. Pat. No. 6,120,766). Since then, the safety and efficacy of Campath-1H has been the focus of several clinical studies in patients with MS (See, e.g.: T. Moreau et al., *Lancet* (1994), 344:298-301; T. Moreau et al., *Brain* (1996), 119:225-237; A. Coles et al., *Ann. Neurol.* (1999), 46:296-304; A. Coles et al. (*Neurology* 60 March 2003 (Suppl. 1); A. Coles et al., *Clinical Neurology and Neurosurgery* (2004), 106:270-274).

Most recently, in the Phase 2 clinical study designated CAMMS223, alemtuzumab was administered at two dose levels (a five day course of 12 mg or 24 mg/day for cumulative doses of 60 or 120 mg in the first year, followed by a three-day course of 12 mg or 24 mg/day for cumulative doses of 36 or 72 mg in the second year, with possible retreatment similarly using 36 or 72 mg in the third year). In an active comparator design, patients on the control arm received interferon beta-1a (Rebif®; EMD Serono, Inc.) 44 mcg subcutaneously (SC) three times per week as indicated in the product label (O'Donnell, L, et al, Presented at the Consortium of Multiple Sclerosis Centers Annual Meeting, Toronto, Canada, Jun. 2-6, 2004; Compston, A., et al., Presented at the $22^{nd}$ meeting of the European Committee for Treatment and Research in Multiple Sclerosis (ECTRIMS), Madrid, Spain. Sep. 27 to 30, 2006; Fox, E., et al., Presented at the ECTRIMS, Madrid, Spain (2006)).

Interim results were derived from pre-specified efficacy and safety interim analyses conducted after one or two years of treatment for all patients in the planned three year trial. They showed that alemtuzumab was more effective than interferon beta-1a (Rebif®; EMD Serono, Inc.), a licensed treatment for MS, in reducing the risk of MS relapse and in slowing the accrual of sustained disability. Specifically, patients treated with either alemtuzumab regimen experienced at least a 75% reduction in the risk for relapse after at least one- and two-years of follow-up when compared to patients treated with interferon beta-1a. The alemtuzumab-treated patients additionally experienced at least a 60% reduction (relative to Rebif®-treated patients) in the risk for the sustained accumulation of disability after 1 year, and at least a 65% reduction in that risk after 2 years.

During pilot studies of alemtuzumab as a treatment for MS, it was noted that a high percentage of individuals developed disorders involving the thyroid gland. The first report of this phenomenon (Coles et al. *Lancet*, 354:1691-95 (1999)) described clinical and laboratory evidence of autoimmune thyroid disease developing in roughly one third of patients (9 of 27) who had previously received alemtuzumab as treatment for their MS. Specifically, these patients had developed antibodies against the thyrotropin receptor and carbimazole-responsive autoimmune hyperthyroidism, and several of them also had episodes characterized as autoimmune thyroiditis. Subsequent studies from the same group (Coles et al., *Neurology,* 60 March 2003, Suppl. 1) and others (Compston, A., et al., Presented at the $22^{nd}$ meeting of the European Committee for Treatment and Research in Multiple Sclerosis (ECTRIMS), Madrid, Spain. Sep. 27 to 30, 2006) have confirmed that thyroid glandular disorders occur with increased frequency following alemtuzumab treatment in patients with MS. Onset of thyroid disorders is typically delayed by several months or years following initial exposure to alemtuzumab.

Delayed onset of thyroid disorders also occurs in other circumstances characterized by lymphocyte depletion and repopulation, notably delayed onset of thyroid disorders following bone marrow transplantation, whether autologous or allogeneic, and whether for treatment of primary immunodeficiency or for reconstitution after iatrogenic bone marrow suppression (Ishiguro H., et al., *J Clin Endocrinol Metab,* 89(12):5981-6 (2004); Slatter M. A., et al., *Bone Marrow Transplant.,* 33(9):949-53 (2004); Carlson K., et al., *Bone Marrow Transplant.,* 10(2):123-7. (1992); Lee W. Y., et al., *Bone Marrow Transplant.,* 28(1):63-6. (2001)). Chemotherapeutic regimens in these cases varied widely. Their chief similarity with the thyroid-disease prone alemtuzumab-treated MS patients is the regeneration of lymphocyte populations from an initial state of natural or iatrogenic depletion.

A scientific understanding of the pathogenesis of thyroid autoimmune disorders that complicate lymphocyte depleting therapies, and the reason for a delay in onset of these disorders, is currently incomplete.

In summary, alemtuzumab appears to be an effective treatment for patients with a variety of disorders, but its use in MS but has been associated with auto-immune complications including thyroid glandular disorders. Similar complications occur with other lymphocyte depleting therapies. In some individuals, the benefit from therapeutic regimens involving lymphocyte depletion may be offset by adverse effects. Thus, in order to maximize the benefit-to-risk ratio attending the use of a lymphocyte depleting therapy such as alemtuzumab in patients (e.g., MS patients), it would be desirable to have a means for identifying (e.g., prior to the initiation of alemtuzumab treatment) those individuals who are at increased risk for autoimmune thyroid disorders. Such prediction of risk would be useful to support informed medical decision making, e.g., whether or not to initiate treatment with a lymphocyte depleting regimen in a given individual based on the predicted risk for this adverse effect.

SUMMARY OF THE INVENTION

The invention relates to a method for predicting the risk for thyroid glandular disorders that may occur in a patient as a complication of therapeutic regimens that deplete lymphocytes (a lymphocyte depleting regimen). The method is based on detecting the presence or absence of autoantibodies in the patient prior to receiving a first or subsequent course of the lymphocyte depleting regimen (e.g., prior assessment of autoantibodies in the blood). For example, blood testing prior to alemtuzumab treatment allows for the prediction of risk for thyroid disorders that can occur following alemtuzumab treatment.

More specifically, the invention is based in part on the discovery that MS patients who have antibodies directed against the thyroid peroxidase enzyme (TPO) prior to or at the time of initial treatment with alemtuzumab are at increased risk for developing thyroid disorders subsequent to such treatment.

Thus, in one embodiment, the invention involves a method of determining patients at relatively higher risk for developing a thyroid disorder subsequent to treatment with a therapeutic regimen that depletes lymphocytes (and also perhaps depletes other cell types), comprising the step of assaying a biological sample from the patient for antibodies directed against thyroid peroxidase (TPOA). Patients who test positive for the predictive autoantibodies are at relatively increased risk for developing a thyroid disorder should they receive treatment with such regimen. Individuals who test negative for the predictive autoantibodies are at relatively lower risk for a thyroid disorder should they receive the treatment.

In another embodiment, the invention involves a method of determining patients at relatively higher risk for developing a thyroid disorder subsequent to treatment with a therapeutic regimen that depletes cells which bear CD52 as a surface marker (i.e., CD52-positive cells), comprising the step of assaying a biological sample from the patient for antibodies directed against thyroid peroxidase (TPOA). Patients who test positive for the predictive autoantibodies are at relatively increased risk for developing a thyroid disorder should they receive treatment with the regimen that depletes CD52-positive cells. Individuals who test negative for the predictive autoantibodies are at relatively lower risk for a thyroid disorder should they receive such treatment.

As used herein a "regimen which depletes CD52-positive cells" includes any molecule which depletes, partially or completely, human cells bearing the CD52 marker. For example, an agent that depletes CD52-positive cells includes, without limitation, an antibody, a small interfering RNA or a small molecule that reduces the count of CD52-bearing cells from blood circulation and/or bodily tissues. The therapeutic regimen that depletes CD52-positive cells will, in particular embodiments, involve administration of an antibody that binds specifically to CD52. In some embodiments, it is a human or a humanized anti-CD52 antibody such as or similar to alemtuzumab (Campath®, MabCampath®, Campath-1H®).

In another embodiment, the invention relates to a method for identifying a patient with multiple sclerosis that is at risk for developing a thyroid disorder subsequent to treatment with a regimen that depletes lymphocytes (e.g., treatment with an agent that depletes CD52-positive cells, such as alemtuzumab), comprising determining whether antibodies directed against thyroid peroxidase are present in the patient, wherein if the antibodies are present in the patient then the patient is at risk for developing a thyroid disorder subsequent to treatment. The methods described herein are applicable to patients with relapsing remitting multiple sclerosis as well as primary and secondary progressive multiple sclerosis.

In another embodiment, the invention involves a method of determining patients at relatively higher risk for developing a thyroid disorder subsequent to treatment, where that treatment involves a therapeutic regimen that produces iatrogenic lymphocyte depletion as an accompaniment to the desired therapeutic effect. Examples of such regimens include, without limitation, those that involve administration of one or more cytotoxic chemotherapy agents as for treatment of neoplasia, autoimmunity, or preparatory to bone marrow or solid organ transplantation; and the administration of anti-thymocyte globulin (e.g., Thymoglobulin®) intended to deplete T lymphocytes for suppression of organ transplant rejection.

It is expected that the methods of the invention will be useful for predicting the risk of a thyroid disorder developing in a patient subsequent to treatment with any therapeutic regimen that depletes lymphocytes, while other cell types may or may not be depleted by the treatment. The total lymphocyte population comprises subsets, chiefly T cells, B cells, and NK cells. In one embodiment, the therapeutic regimen that depletes lymphocytes is a regimen targeted against T lymphocytes. In another embodiment, it is a regimen targeted against B lymphocytes. In another embodiment, it is a regimen targeted against NK cells. In other embodiments, it is a regimen targeted against various combinations of T and B lymphocytes and NK cells (e.g., T and B and NK; T and B but not NK; etc.).

Foreknowledge of the risk for developing thyroid disorders associated with lymphocyte depletion is useful to support informed medical decision making, e.g., whether or not to initiate treatment with a lymphocyte depleting regimen in a given patient based on the predicted risk for the development of a thyroid disorder.

Tests to determine whether antibodies directed against thyroid peroxidase are present in the patient may be performed prior to, or after, treatment with the regimen that depletes lymphocytes. Ideally, the test for TPOA is performed prior to a given course of treatment so that knowledge of the potential risks of treatment may be considered by the doctor and patient in making treatment decisions. However, knowledge of the presence of TPOA is also useful subsequent to treatment as an early indicator for increasing risk.

Autoimmune thyroid disorders that may occur as a result of treating a patient with a lymphocyte depleting therapy may manifest as either hypothyroidism or hyperthyroidism. Common diagnoses include Graves' Disease (also known as diffuse toxic goiter, von Basedow's disease, or Parry's disease) and autoimmune thyroiditis (also known as silent thyroiditis or Hashimoto's thyroiditis) and combinations thereof.

Antibodies directed against thyroid peroxidase are usually sought in a blood sample (commonly serum or plasma) obtained from the patient, but might be detected in any biological sample obtained from the patient, including lymph, urine and/or tissue.

As one of skill in the art will understand the particular method used to detect the presence of antibodies against TPO is not a limiting feature of the invention. Various methods for detecting antibodies directed against thyroid peroxidase are well known to those of skill in the art. Such methods include the use of enzyme-linked immunosorbent assays (ELISA), radioimmunoassays (RIA), hemagglutination assays and various other techniques that employ a form or fragment of the thyroid peroxidase protein as a target intended to attract and bind to the antibodies to be measured, and employing any method appropriate to detect and perhaps quantitate the bound antibodies. The various methods described above and other similar methods may also be employed to detect antibodies reactive with thyroid microsomes, a tissue fraction that is enriched in the thyroid peroxidase enzyme protein, to yield an equivalent diagnostic result. Anti-microsomal antibodies are essentially equivalent to TPOA. Other methods involve measurement of TPO enzyme activity, with the presence and concentration of TPOA inferred by inhibition of TPO enzyme activity

DETAILED DESCRIPTION OF THE INVENTION

CAMMS223 is the name for a Phase 2 clinical trial investigating the safety and efficacy of two dose levels of alemtuzumab in comparison with interferon beta-1a (Rebif®) in the treatment of patients with early, active, relapsing-remitting MS. Patients referred for participation in CAMMS223 were screened for anti-thyroid-stimulating hormone (TSH)-receptor antibodies (hereafter, TSHRA) before entry and excluded if positive. Patients were also tested for anti-thyroid peroxidase antibodies (hereafter, TPOA) but this did not influence their eligibility or treatment. In total, 334 patients were randomized to IFN-beta-1a (44 mcg SC thrice weekly), or alemtuzumab high-dose (24 mg/day intravenously (IV)) or low-dose (12 mg/day IV). Alemtuzumab was given daily for 5 days at Month 0 and for 3 days at Month 12 and, for some patients, again at Month 24.

During the next 3 years, thyroid-related adverse events were tallied, and all patients had thyroid-related hormones and thyroid autoantibodies tested at regular intervals: TSH, L-thyroxine (T3) and L-triiodothyronine (T4) and TSHRA were tested quarterly, and thyroid peroxidase antibody (TPOA) were tested twice yearly. TPOA were tested using a commercially available kit, Varelisa TPO antibodies, manufactured by Sweden Diagnostics and distributed by Somagen, catalogue number 12396 (test protocol described in Example 1).

One focus of the analyses was the correlation among abnormalities on several thyroid-related laboratory parameters. Interim analysis was conducted with 2.2 years median follow-up ($1^{st}$ quartile=2.0; $3^{rd}$=2.5). Thyroid-related adverse events (AEs) and laboratory abnormalities occurred in all 3 treatment arms (see Compston et al., 2006, op cit.).

According to the interim analysis cited above, the proportion of alemtuzumab-treated patients with thyroid clinical AEs was 11.1% versus 1.9% in patients who had received IFN-beta-1a. More thyroid AEs occurred in the low-dose arm but this difference between alemtuzumab doses was not significant. Graves' disease or hyperthyroidism was reported in 14/216 alemtuzumab-treated patients (6.5%), and in 0/106 IFN-beta-1a-treated patients (p<0.0001). TSHRA were found in 47/216 (21.8%) patients after alemtuzumab and 2/103 (1.9%) after IFN-beta-1a. Laboratory markers of thyroid autoimmunity (TSHRA and/or TPOA) occurred without clinical thyroid AEs in 16.7% of patients after treatment with alemtuzumab versus 11.3% of patients treated with IFN-beta-1a.

As described herein, these thyroid-related events were examined in the context of baseline (pre-treatment) laboratory assessments (see Example 1). It was found that thyroid clinical AEs were reported for 17/176 alemtuzumab-treated patients (9.7%) who tested negative for TPOA at baseline versus 5/16 patients (31.1%) who tested initially positive (relative risk=3.2, p=0.029), and for 2/87 IFN-beta-1a treated patients (2.3%) who tested negative for TPOA at baseline versus 0/3 patients (0%) who tested initially positive. Strikingly, TSHRA developed in only 24/176 alemtuzumab-treated patients (13.6%) who tested negative for TPOA at baseline versus 9/16 patients (56.3%) who initially tested positive (relative risk=4.1, p<0.0001), and in 2/87 IFN-beta-1a-treated patients (2.3%) who tested negative for TPOA at baseline versus 0/3 patients (0%) who initially tested positive.

Thus, in a retrospective analysis among MS patients treated with alemtuzumab, individuals who had antibodies directed against TPO at the time of or prior to their initial exposure to alemtuzumab were at 3- or 4-fold increased risk for subsequent thyroid disorders when compared with individuals who at baseline had tested negative for anti-TPO antibodies.

It should be noted that most patients who did develop thyroid abnormalities on study had tested TPOA negative at entry. Thus, the TPOA test appears to have a fairly high specificity but low sensitivity. This could reflect poor TPOA assay sensitivity or may indicate that some patients are at risk for alemtuzumab-related thyroid disorders despite an absence of TPOA at baseline.

Accordingly, the invention encompasses methods for identifying a patient that is at risk for developing a thyroid disorder subsequent to treatment with a regimen that depletes lymphocytes, comprising determining whether antibodies directed against thyroid peroxidase are present in the patient, wherein if the antibodies are present in the patient then the patient is at risk for developing a thyroid disorder subsequent to treatment.

Lymphocytes are white blood cells formed in lymphatic tissue of an individual and divided into three principle groups: T cells, B cells, and NK cells. Thus, in one aspect, the regimen depletes T cells. In another aspect, the regimen depletes B cells. In another aspect, the regimen depletes NK cells. In yet another aspect, the regimen depletes various combinations of T and B and NK cells. The regimen includes any treatment plan that results in a partial or complete deletion of a patient's lymphocytes during or after treatment. In one embodiment, the regimen comprises the administration of one or more cytotoxic agents (e.g., drugs). In one embodiment, the regimen comprises administration of an agent that depletes cells expressing CD52 as a cell surface marker (i.e., CD52-positive cells).

Thus, in one embodiment, the invention encompasses methods for identifying a patient that is at risk for developing a thyroid disorder subsequent to treatment with an agent that depletes CD52-positive cells, comprising determining whether antibodies directed against thyroid peroxidase are present in the patient, wherein if the antibodies are present in the patient then the patient is at risk for developing a thyroid disorder subsequent to treatment.

In a particular aspect, the invention relates to a method for identifying an MS patient that is at risk for developing a thyroid disorder subsequent to treatment with an agent that depletes CD52-positive cells, comprising determining whether antibodies directed against thyroid peroxidase are present in the patient, wherein if the antibodies are present in the patient then the patient is at risk for developing the thyroid disorder.

As used herein a "regimen which depletes CD52-positive cells" includes any regimen which depletes, partially or completely, human cells bearing the CD52 marker. For example, a regimen that depletes CD52-positive cells includes, without limitation, administration of an antibody, a small interfering RNA or a small molecule that reduces the count of CD52-bearing cells from blood circulation and/or bodily tissues.

In a particular embodiment, an agent that depletes CD52-positive cells is an antibody that is specific for CD52. An antibody that is specific for CD52 is a molecule that selectively binds to CD52 but does not substantially bind to other molecules in a sample, e.g., in a biological sample that contains CD52. The term "antibody," as used herein, refers to an immunoglobulin or a part thereof, and encompasses any polypeptide comprising an antigen-binding site regardless of the source, method of production, and other characteristics. The term includes but is not limited to polyclonal, monoclonal, monospecific, polyspecific, humanized, human, single-chain, chimeric, synthetic, recombinant, hybrid, mutated, conjugated and CDR-grafted antibodies. The term "antigen-binding site" refers to the part of an antibody molecule that comprises the area specifically binding to or complementary to, a part or all of an antigen. An antigen-binding site may comprise an antibody light chain variable region ($V_L$) and an antibody heavy chain variable region ($V_H$). An antigen-binding site may be provided by one or more antibody variable domains (e.g., an Fd antibody fragment consisting of a $V_H$ domain, an Fv antibody fragment consisting of a $V_H$ domain and a $V_L$ domain, or an scFv antibody fragment consisting of a $V_H$ domain and a $V_L$ domain joined by a linker). The term "anti-CD52 antibody," or "antibody against CD52," refers to any antibody that specifically binds to at least one epitope of CD52.

The various antibodies and portions thereof can be produced using any of a variety of techniques (see, e.g., Kohler and Milstein, Nature 256:495-497 (1975); Current Protocols in Immunology, Coligan et al., (eds.) John Wiley & Sons, Inc., New York, N.Y. (1994); Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1; Newman, R. et al., *BioTechnology,* 10: 1455-1460 (1992); Ladner et al., U.S. Pat. No. 4,946,778; Bird, R. E. et al., *Science,* 242: 423-426 (1988)).

In a particular embodiment, the CD52 antibody is alemtuzumab, a recombinant DNA-derived humanized monoclonal antibody that is directed against CD52. The sequence of alemtuzumab (Campath-1H®), including the sequence of the three CDRs contained therein, is disclosed in U.S. Pat. No. 5,846,534, wherein a humanized antibody which binds effectively to the antigen CD52 as well as a method of treating a human patient having a lymphoid malignancy with such an antibody is described. Procedures for preparation and testing of such an antibody are also disclosed.

In addition to multiple sclerosis (both relapsing-remitting and primary and secondary progressive), conditions that have been treated with alemtuzumab include hematologic malignancies such as B-cell chronic lymphocytic leukaemia (B-CLL), non-Hodgkin's lymphoma and leukemias, as well as a variety of immune mediated disorders including graft-versus-host disease, organ transplant rejection, vasculitis, uveitis, scleroderma, autoimmune cytopenias and rheumatoid arthritis. However, the method of the invention is not limited to being performed on patients with these particular diseases. Rather, it is useful for patients with any disease, so long as such disease is amenable to treatment with an agent that depletes lymphocytes, and such treatment correlates with the development, in at least some patients, of a thyroid disorder.

Autoimmune thyroid disorders that may occur as a result of treating a patient with a lymphocyte depleting therapy may manifest as either hypothyroidism or hyperthyroidism. Common diagnoses include Graves' Disease (also known as diffuse toxic goiter, von Basedow's disease, or Parry's disease) and autoimmune thyroiditis (also known as silent thyroiditis or Hashimoto's thyroiditis) and combinations thereof.

Tests to determine whether antibodies directed against thyroid peroxidase are present in a patient may be performed prior to, or after, treatment with the lymphocyte depleting regimen. Ideally, the presence of antibodies is determined prior to an initial course of treatment so that knowledge of the potential risks of treatment may be considered by the doctor and patient and weighed against the benefits of treatment. However, it will also be useful to perform the methods of the invention subsequent to the initial treatment of a patient, e.g., in order to determine the risk/benefit of a subsequent course of treatment or in order to monitor for any increasing risk of development of a thyroid disorder at any time subsequent to treatment.

A variety of methods for detecting antibodies directed against thyroid peroxidase are known to those of skill in the art. In a particular embodiment, an enzyme-linked immunosorbent assay (ELISA) can be used (Premawardhana, L. et al., *J. Clin. Endocrinol. Metab.,* 85:71-75 (2000); Stagnaro-Green, A., et al., *J. Clin. Endocrinol Metab.,* 74(3):645-653 (1992)). In a common application of this method, a plastic substrate is coated with standardized amount of purified thyroid peroxidase enzyme protein. The blood sample to be analyzed is precisely diluted and applied to the coated substrate for a period of time, during which TPOA antibodies in the blood sample will bind to the plastic because of their interaction with the TPO adherent to this substrate. Following a standardized washing step to remove all blood components that fail to bind to TPO, a reagent is added that will recognize and stick to any bound antibody, notably including TPOA. This reagent is engineered to have a dual function: in addition to binding with antibodies, it can provide a signal (usually chromogenic or chemiluminescent) in proportion to the amount bound. Thus, the signal indicates indirectly the amount of TPOA in the original sample.

A variety of methods for detecting antibodies directed against thyroid peroxidase are known to those of skill in the art, and some have been widely used, such as radioimmunoassay (Kung, V. T. et al., *Clin. Chem.,* 27(1):39-42(1981); haemagglutination assay (Marazuela, et al, supra); and the Immulite 2000 Anti-TPO Ab immunoassay with chemiluminescent detection, sold by Siemens Medical Solutions Diagnostics. These and various other techniques have in common that they employ a form or fragment of the thyroid peroxidase protein as a target intended to attract and bind to the antibodies to be measured, and employing any method appropriate to detect and perhaps quantitate the bound antibodies. In another embodiment, the various methods described above and other similar methods are employed to detect antibodies reactive with thyroid microsomes, a tissue fraction that is enriched in the thyroid peroxidase enzyme protein.

In the methods of the present invention, the presence of antibodies directed against thyroid peroxidase in a patient can be determined by assaying a biological sample obtained from the patient. As used herein a "sample" includes any suitable biological sample which could include antibodies directed against thyroid peroxidase. For example, a sample includes tissues, cells, biological fluids and extracts thereof obtained (e.g., isolated) from an individual. Biological fluids include blood (e.g., whole blood, packed red blood cells), serum, plasma, lymph, urine and semen.

The methods described herein can further comprise comparing the amount (level, titer) of antibodies directed against thyroid peroxidase (TPOA) present in the patient to the amount of TPOA in a suitable control sample. For example, the control sample may be taken from an individual who is not believed to be at risk for developing a thyroid disorder (e.g., a sample from a healthy individual). Alternatively, the control sample could be taken from a patient with the same or similar disease condition who is administered an alternative treatment regimen which is not lymphocyte depleting, which alternative regimen is not associated with an increased risk of thyroid disorders. Alternatively, the measurement of TPOA may be compared with a validated standard not based on a control biological sample, e.g., a diluent or other solution not expected to yield a positive test result.

The following Examples provide illustrative embodiments of the invention. One of ordinary skill in the art will recognize the numerous modifications and variations that may be performed without altering the spirit or scope of the present invention. Such modifications and variations are encompassed within the scope of the invention. The Examples do not in any way limit the invention.

EXAMPLE 1

Method for Assay of Antibodies Reactive with Thyroid Peroxidase

A qualititative method involving an indirect non-competitive enzyme immunoassay specific for the TPO protein was employed for the TPOA measurements described in Example 2. The method involved the use of a commercially available kit (Varelisa) TPO antibodies test, manufactured by Phadia GmbH (formerly Sweden Diagnostics) and distributed by Somagen, catalogue number 12396. In brief, patient serum samples were diluted 1/100 using the provided diluent, and 100 microliters of diluted sample was placed into a plastic well previously coated with purified TPO protein. The sample was allowed to incubate for 30 minutes, and then washed 3-5 times with 300 microliters of provided wash solution. To each well was then added 100 microliters of a provided reagent that incorporates the enzyme horse-radish peroxidase (HRP) covalently linked to an anti-immunoglobulin G (IgG) isotype-specific antibody. Following another 30 minute incubation step, the conjugate was washed 3-5 times with 300 microliters of provided wash solution. To each well was then added 100 microliters of solution containing 3,3',5,5'-tetramethylbenzidine, which is an effective substrate for a chemical reaction catalyzed by HRP that generates a visible colorimetric signal in proportion to the amount of adherent HRP conjugate and the duration of the reaction. Following a 10 minute incubation step, the colorimetric reaction was terminated by addition of 50 microliters of a sulfuric acid solution. The colorimetric signal was measured using a spectrophotometer to determine the absorbance at a wavelength of 450 nm between 10 to 30 minutes after addition of the sulfuric acid solution. The results were interpreted qualitatively as either negative (absorbance of positive control/absorbance of sample<1), positive (absorbance of positive control/absorbance of sample>1.4), or equivocal (ratio>1.0<1.4).

EXAMPLE 2

Autoantibody Prediction of Risk for Thyroid Adverse Events After Alemtuzumab Treatment for Relapsing Remitting Multiple Sclerosis (RRMS)

The objective of this study was to examine pre-treatment thyroid peroxidase antibodies (TPOA) as a predictor of risk for alemtuzumab-related autoimmune thyroid disorders within 2 years of first drug exposure. In connection with the CAMMS223 clinical trial, described supra, TSH, free T3, free T4, and TSHRA were tested quarterly, and anti-thyroid peroxidase (TPOA) twice yearly in all patients, using the testing protocol and kit described in Example 1.

As set forth in the table below, with 2.2 years median follow-up, thyroid AEs were reported for 17/176 alemtuzumab-treated patients (9.7%) who tested negative for TPOA at baseline versus 5/16 patients (31.1%) who tested initially positive (RR=3.2, p=0.029), and for 2/87 IFN-beta-1a treated patients (2.3%) who tested negative for TPOA at baseline versus 0/3 patients (0%) who tested initially positive. Strikingly, TSHRA developed in only 24/176 alemtuzumab-treated patients (13.6%) who tested negative for TPOA at baseline versus 9/16 patients (56.3%) who initially tested positive (RR=4.1, p<0.0001), and in 2/87 IFN-beta-1a-treated patients (2.3%) who tested negative for TPOA at baseline versus 0/3 patients (0%) who initially tested positive.

TABLE 1

|  |  | Number | % |
|---|---|---|---|
| Evaluable Alemtuzumab Patients |  | 192 | 100 |
| Baseline anti TPO− |  | 176 | 91.7 |
|  | Thyroid AE | 17 of 176 | 9.7 |
|  | TSH-R Ab | 24 of 176 | 13.6 |
| Baseline anti TPO+ |  | 16 | 8.3 |
|  | Thyroid AE | 5 of 16 | 31.3 |
|  | TSH-R Ab | 9 of 16 | 56.3 |

It is apparent from these data that the presence of TPOA at baseline likely confers increased risk for thyroid disorders after treatment with alemtuzumab.

EXAMPLE 3

Autoantibody Prediction of Risk for Thyroid Adverse Events After Alemtuzumab Treatment for Relapsing Remitting Multiple Sclerosis (RRMS)

The preliminary analysis of data from CAMMS223, presented in Example 2, was extended by analysis of data from the same trial after 3 years median follow-up. As set forth in the table below, thyroid AEs developing within 3 years from first alemtuzumab exposure were reported for 35/182 alemtuzumab-treated patients (19.2%) who tested negative for TPOA at baseline versus 8/16 patients (50%) who tested initially positive (RR=2.60, p=0.0087), and for 2/93 IFN-beta-1a treated patients (2.2%) who tested negative for TPOA at baseline versus 0/6 patients (0%) who tested initially positive. Strikingly, TSHRA developed in only 46/182 alemtuzumab-treated patients (25.3%) who tested negative for TPOA at baseline versus 10/16 patients (62.5%) who initially tested positive (RR=2.47, p<0.0031), and in 2/93 IFN-beta-1a-treated patients (2.2%) who tested negative for TPOA at baseline versus 0/3 patients (0%) who initially tested positive.

TABLE 2

|  |  | Number | % |
|---|---|---|---|
| Evaluable Alemtuzumab Patients |  | 198 | 100 |
| Baseline anti TPO− |  | 182 | 91.9 |
|  | Thyroid AE | 35 of 182 | 19.2 |
|  | TSH-R Ab | 46 of 182 | 25.3 |
| Baseline anti TPO+ |  | 16 | 8.1 |
|  | Thyroid AE | 8 of 16 | 50 |
|  | TSH-R Ab | 10 of 16 | 62.5 |

These longer-term data continue to support the conclusion that presence of TPOA at baseline likely confers increased risk for thyroid disorders after treatment with alemtuzumab.

All publications, including patents, cited in this disclosure are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for treating a multiple sclerosis (MS) patient, comprising:
   (a) selecting an MS patient for treatment with an anti-CD52 antibody, wherein a biological sample obtained from the patient prior to the treatment has tested negative for antibodies against thyroid peroxidase or thyroid microsomes; and
   (b) administering the anti-CD52 antibody to the patient.

2. The method of claim 1, wherein the patient has relapsing remitting multiple sclerosis (MS).

3. The method of claim 1 or 2, wherein the anti-CD52 antibody is alemtuzumab.

4. The method of claim 1 or 2, wherein the anti-CD52 antibody comprises one or more CDRs having an amino acid sequence identical to the amino acid sequence of a CDR of alemtuzumab.

5. The method of claim 1, wherein the thyroid disorder is selected from the group consisting of: hypothyroidism, hyperthyroidism, Graves' disease, autoimmune thyroiditis and a combination thereof.

* * * * *